US009393146B2

(12) United States Patent  (10) Patent No.: US 9,393,146 B2
Gaylord  (45) Date of Patent: Jul. 19, 2016

(54) ANKLE STABILIZING DEVICE COMPRISING AN ABOVE-THE-FOOT BODY MEMBER AND INTEGRATED FLEXIBLE NON-STRETCH ANKLE BELT

(71) Applicant: Medical Specialties Incorporated, Charlotte, NC (US)

(72) Inventor: Eric Lee Gaylord, Weddington, NC (US)

(73) Assignee: Medical Specialties, Incorporated, Charlotte, NC (US)

( * ) Notice: Subject to any disclaimer, the term of this patent is extended or adjusted under 35 U.S.C. 154(b) by 0 days.

(21) Appl. No.: 13/954,305

(22) Filed: Jul. 30, 2013

(65) Prior Publication Data

US 2014/0188026 A1    Jul. 3, 2014

Related U.S. Application Data

(63) Continuation-in-part of application No. 13/758,311, filed on Feb. 4, 2013, which is a continuation-in-part of application No. 12/062,621, filed on Apr. 4, 2008, now Pat. No. 8,721,578.

(60) Provisional application No. 61/794,214, filed on Mar. 15, 2013, provisional application No. 61/633,041, filed on Feb. 3, 2012.

(51) Int. Cl.
*A61F 5/00*    (2006.01)
*A61F 5/01*    (2006.01)

(52) U.S. Cl.
CPC .................................... *A61F 5/0111* (2013.01)

(58) Field of Classification Search
CPC .... A61F 5/0111; A61F 5/0116; A61F 5/0113
USPC .......................... 602/5, 27–29, 60–66, 27–9; D24/190–192; 128/882, 27–9, 65–66
See application file for complete search history.

(56) References Cited

U.S. PATENT DOCUMENTS

| 3,308,829 | A | * | 3/1967 | Edwards | 36/142 |
| 3,926,186 | A | | 12/1975 | Nirschl | |
| 4,433,682 | A | | 2/1984 | Badra | |
| 4,926,846 | A | | 5/1990 | Nassar | |
| 5,067,486 | A | * | 11/1991 | Hely | 602/27 |
| 5,090,404 | A | * | 2/1992 | Kallassy | 602/65 |
| 5,795,316 | A | | 8/1998 | Gaylord | |
| 6,540,705 | B2 | | 4/2003 | Norstrem et al. | |
| 6,652,474 | B1 | * | 11/2003 | Quinn et al. | 602/21 |
| 7,651,472 | B2 | | 1/2010 | Gaylord et al. | |
| 7,753,865 | B1 | * | 7/2010 | Hely | 602/23 |
| 7,828,758 | B2 | | 11/2010 | Clements et al. | |
| D639,965 | S | | 6/2011 | Wehsely-Swiczinsky | |

(Continued)

*Primary Examiner* — Kim M Lewis
(74) *Attorney, Agent, or Firm* — Schwartz Law Firm, P.C.

(57) ABSTRACT

An ankle stabilizing device is designed for use on an ankle and foot of a wearer. The ankle stabilizing device includes an above-the-foot flexible body member designed to substantially encircle the ankle. The body member has an open upper end adapted for extending to a point above the ankle. An elongated, flexible, non-stretch ankle belt is secured to the body member proximate its upper end, and is adapted for extending circumferentially around a lower leg of the wearer. At least one elongated flexible stabilizing strap has a proximal end affixed to the body member, and an opposing free end adapted for extending under the foot and releasably attaching to the body member.

9 Claims, 17 Drawing Sheets

(56) References Cited

U.S. PATENT DOCUMENTS

| | | |
|---|---|---|
| 7,993,295 B2 | 8/2011 | Nelson |
| D649,650 S | 11/2011 | Weaver, II et al. |
| D649,651 S | 11/2011 | Weaver, II et al. |
| 2004/0078999 A1 | 4/2004 | Freed |
| 2006/0004311 A1* | 1/2006 | Hargrave .............. A61F 5/0111 602/5 |
| 2009/0112140 A1 | 4/2009 | Gaylord et al. |
| 2013/0012855 A1 | 1/2013 | Giza et al. |

* cited by examiner

ANKLE STABILIZING DEVICE COMPRISING AN ABOVE-THE-FOOT BODY MEMBER AND INTEGRATED FLEXIBLE NON-STRETCH ANKLE BELT

TECHNICAL FIELD AND BACKGROUND OF THE INVENTION

This invention relates broadly and generally to orthotics including the design, manufacture and application of orthoses; and more specifically, to orthopedic braces adapted for stabilizing the ankle of a wearer. In exemplary embodiments described herein, the present disclosure comprises an ankle stabilizing orthosis incorporating an above-the-foot body member and an integrated flexible non-stretch ankle belt (or "rib").

Numerous examples of orthopedic ankle braces exist in the prior art some of which are described in Applicant's prior issued U.S. Pat. Nos. 7,651,472, 5,795,316, and 5,067,486, and pending U.S. Application Publication No. 2009/0112140 (hereinafter collectively, "Applicant's Prior Patents").

SUMMARY OF EXEMPLARY EMBODIMENTS

Various exemplary embodiments of the present invention are described below. Use of the term "exemplary" means illustrative or by way of example only, and any reference herein to "the invention" is not intended to restrict or limit the invention to exact features or steps of any one or more of the exemplary embodiments disclosed in the present specification. References to "exemplary embodiment," "one embodiment," "an embodiment," "various embodiments," and the like, may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

It is also noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

According to one exemplary embodiment, the present disclosure comprises an ankle stabilizing device for use on an ankle and foot of a wearer. The ankle stabilizing device comprises an above-the-foot flexible body member designed to substantially encircle the ankle. The body member has an open upper end adapted for extending to a point above the ankle. An elongated, flexible, non-stretch ankle belt is secured to the body member proximate its upper end, and is adapted for extending circumferentially (partially or entirely) around a lower leg of the wearer (e.g., above the ankle joint). At least one elongated flexible stabilizing strap has a proximal end affixed to the body member, and an opposing free end adapted for extending under the foot and releasably attaching to the body member.

According to another exemplary embodiment, the flexible body member comprises first and second integrally-formed cooperating side panels adapted for wrapping around the ankle of the wearer.

According to another exemplary embodiment, means are provided for adjustably closing a longitudinal gap between the first and second side panels, thereby adjustably fitting the body member to the ankle of the wearer.

According to another exemplary embodiment, a perforated tongue resides at the longitudinal gap between the first and second side panels.

According to another exemplary embodiment, the means for adjustably closing comprises at least one lace.

According to another exemplary embodiment, the first and second side panels comprise a plurality of eyelets for receiving the lace.

According to another exemplary embodiment, first and second cooperating outside binding straps are attached at a rear of the body member, and are adapted for temporarily covering the releasably attached free end of the stabilizing strap and adjustably encircling the ankle of the wearer.

According to another exemplary embodiment, the ankle belt has a thickness in the range of approximately 1/32 to approximately 1/16 inches, and a width in the range of approximately 1/4 to approximately 3/8 inches.

According to another exemplary embodiment, the ankle belt is affixed to the body member at respective opposite ends of the ankle belt.

According to another exemplary embodiment, respective opposite ends of the ankle belt are slightly arcuate and downwardly turned.

In yet another exemplary embodiment, the present disclosure comprises a method for reducing distal migration of an ankle stabilizing device during wear. The method includes applying the ankle stabilizing device to a lower leg of a wearer. The ankle stabilizing device is then tightened on the lower leg, such that an elongated flexible non-stretch ankle belt extends substantially circumferentially (partially or entirely) around the lower leg—e.g., above the ankle joint. Enhanced circumferential compression is applied by the ankle stabilizing device at the lower leg of the wearer in an area of the ankle belt.

The term "foot" as used herein refers to the terminal part of the leg generally below the ankle joint (talus), and including areas adjacent the calcaneous, plantar fascia, metatarsals, and phalanges. In the exemplary embodiment, except for the stabilizing strap(s) no portion of the ankle stabilizing device covers the foot of the wearer. In other words, only a single thickness of each stabilizing strap resides adjacent an area of the foot.

The term "ankle" refers the terminal part of the lower leg extending generally upwardly from and including the ankle joint.

The term "orthosis" refers broadly herein to any orthopedic appliance, device, or apparatus used to support, align, or improve the function of movable parts of the body; or to prevent or correct deformities involving movable parts of the body.

BRIEF DESCRIPTION OF THE DRAWINGS

Exemplary embodiments of the present invention will hereinafter be described in conjunction with the following drawing figures, wherein like numerals denote like elements, and wherein.

DESCRIPTION OF EXEMPLARY EMBODIMENTS AND BEST MODE

The present invention is described more fully hereinafter with reference to the accompanying drawings, in which one or more exemplary embodiments of the invention are shown. This invention may, however, be embodied in many different forms and should not be construed as limited to the embodiments set forth herein; rather, these embodiments are provided so that this disclosure will be operative, enabling, and complete. Accordingly, the particular arrangements disclosed are meant to be illustrative only and not limiting as to the scope of the invention, which is to be given the full breadth of the appended claims and any and all equivalents thereof. Moreover, many embodiments, such as adaptations, variations, modifications, and equivalent arrangements, will be implicitly disclosed by the embodiments described herein and fall within the scope of the present invention.

Although specific terms are employed herein, they are used in a generic and descriptive sense only and not for purposes of limitation. Unless otherwise expressly defined herein, such terms are intended to be given their broad ordinary and customary meaning not inconsistent with that applicable in the relevant industry and without restriction to any specific embodiment hereinafter described. As used herein, the article "a" is intended to include one or more items. Where only one item is intended, the term "one", "single", or similar language is used. When used herein to join a list of items, the term "or" denotes at least one of the items, but does not exclude a plurality of items of the list.

For exemplary methods or processes of the invention, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present invention.

Additionally, any references to advantages, benefits, unexpected results, or operability of the present invention are not intended as an affirmation that the invention has been previously reduced to practice or that any testing has been performed. Likewise, unless stated otherwise, use of verbs in the past tense (present perfect or preterit) is not intended to indicate or imply that the invention has been previously reduced to practice or that any testing has been performed.

Figure 1:
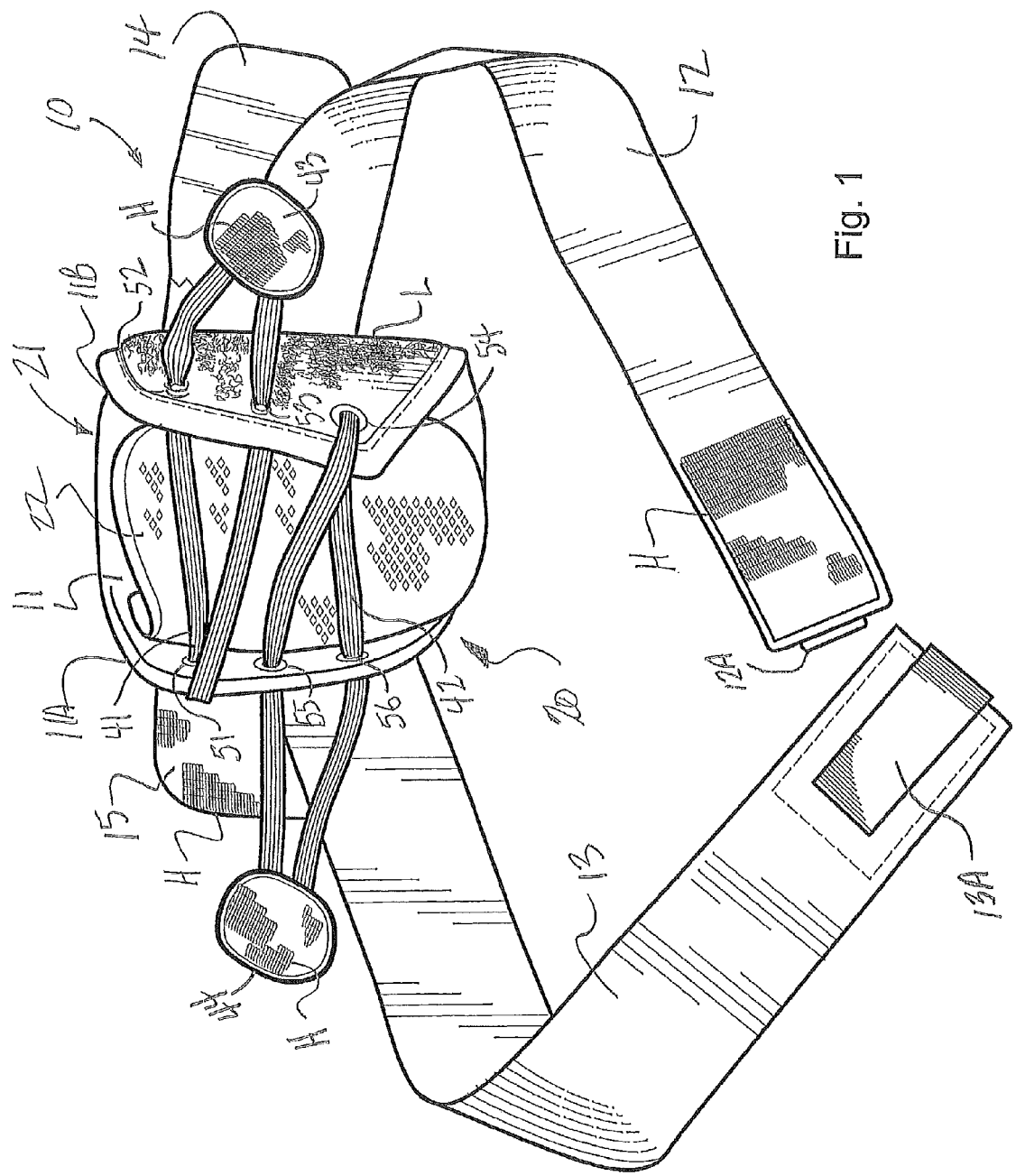
FIG. 1 is a perspective view of an ankle stabilizing device according to one exemplary embodiment of the present disclosure.
Figure 2:
FIGS. 2 and 3 are perspective views of the exemplary ankle stabilizing device applied to an ankle and foot of a wearer.
Figure 3:
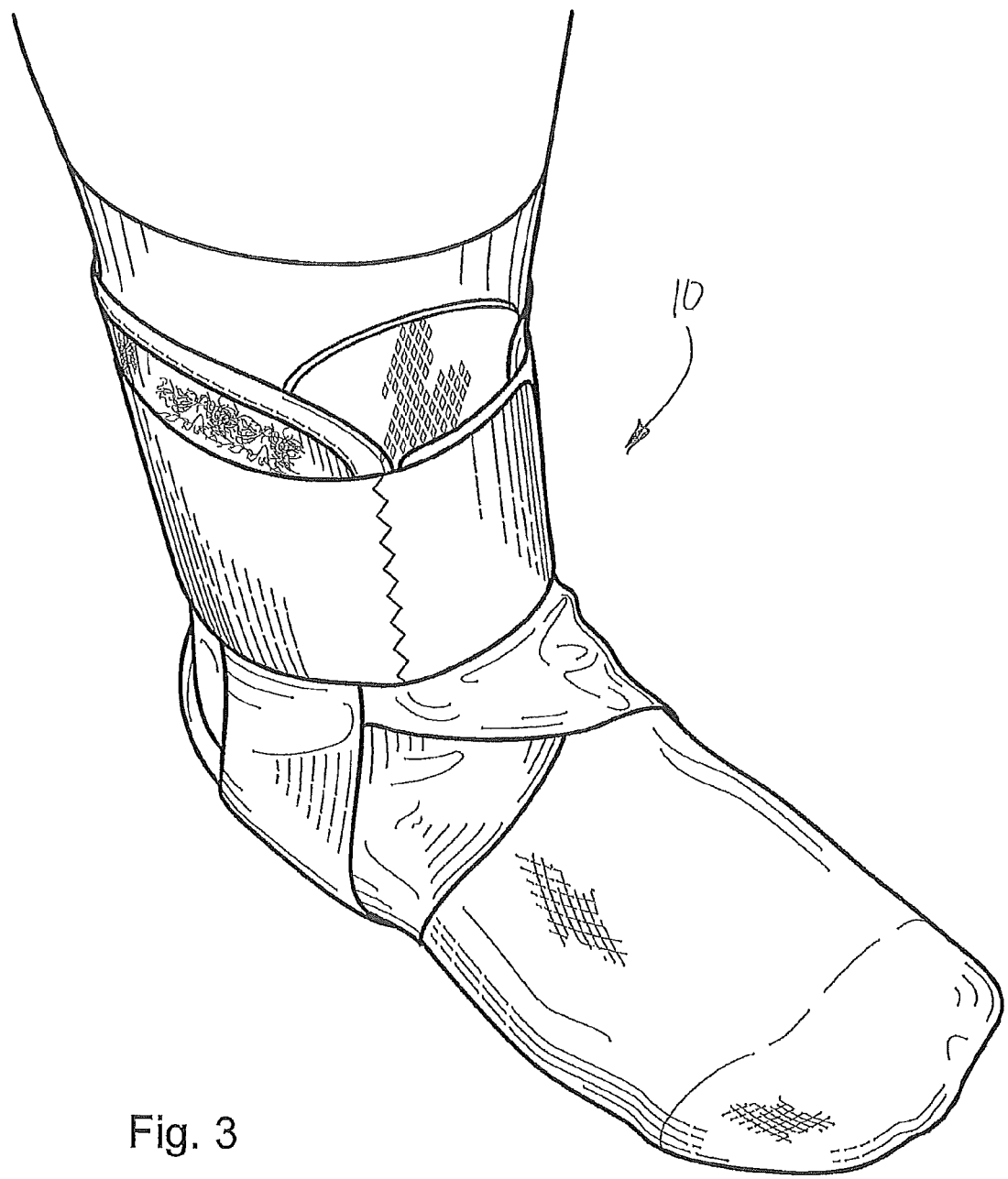

Referring now specifically to the drawings, an ankle stabilizing device according to one exemplary embodiment of the present disclosure is illustrated in FIG. 1, and shown generally at broad reference numeral 10. The exemplary ankle stabilizing device 10 comprises a flexible around-the-ankle body member 11, a pair of non-stretch nylon stabilizing straps 12, 13 attached at the rear (or other portion) of body member 11, and elastic rear-attached binding straps 14, 15. The stabilizing straps 12, 13 and binding straps 14, 15 may be constructed, attached, and assembled as described in any one or more of Applicant's Prior Patents referenced above. The flexible body member 11 may be constructed of a substantially inelastic, multiple-layer woven ballistic nylon fabric (or other material described in Applicant's Prior Patents). The body member 11 defines top and bottom open ends for receiving the foot of a wearer, as describe further below, and a lace-cinch closure assembly 20. The closure assembly 20 functions to adjustably close a longitudinal front gap 21 (or divide) formed between opposing integrally-formed side panels 11A, 11B of body member 11, thereby adjustably tightening the body member 11 around the ankle. A perforated double, warp-knit, three-dimensional fabric tongue 22 may be attached to the body member 11 (extending between side panels 11A, 11B), and adapted to reside between the closure assembly 20 and ankle. FIGS. 2 and 3 show the exemplary ankle stabilizing device 10 applied to the ankle and foot of the wearer. The device 10 may be used over a thin sock or stocking (as shown), or may be applied directly to a bare ankle and foot.

Figure 4:
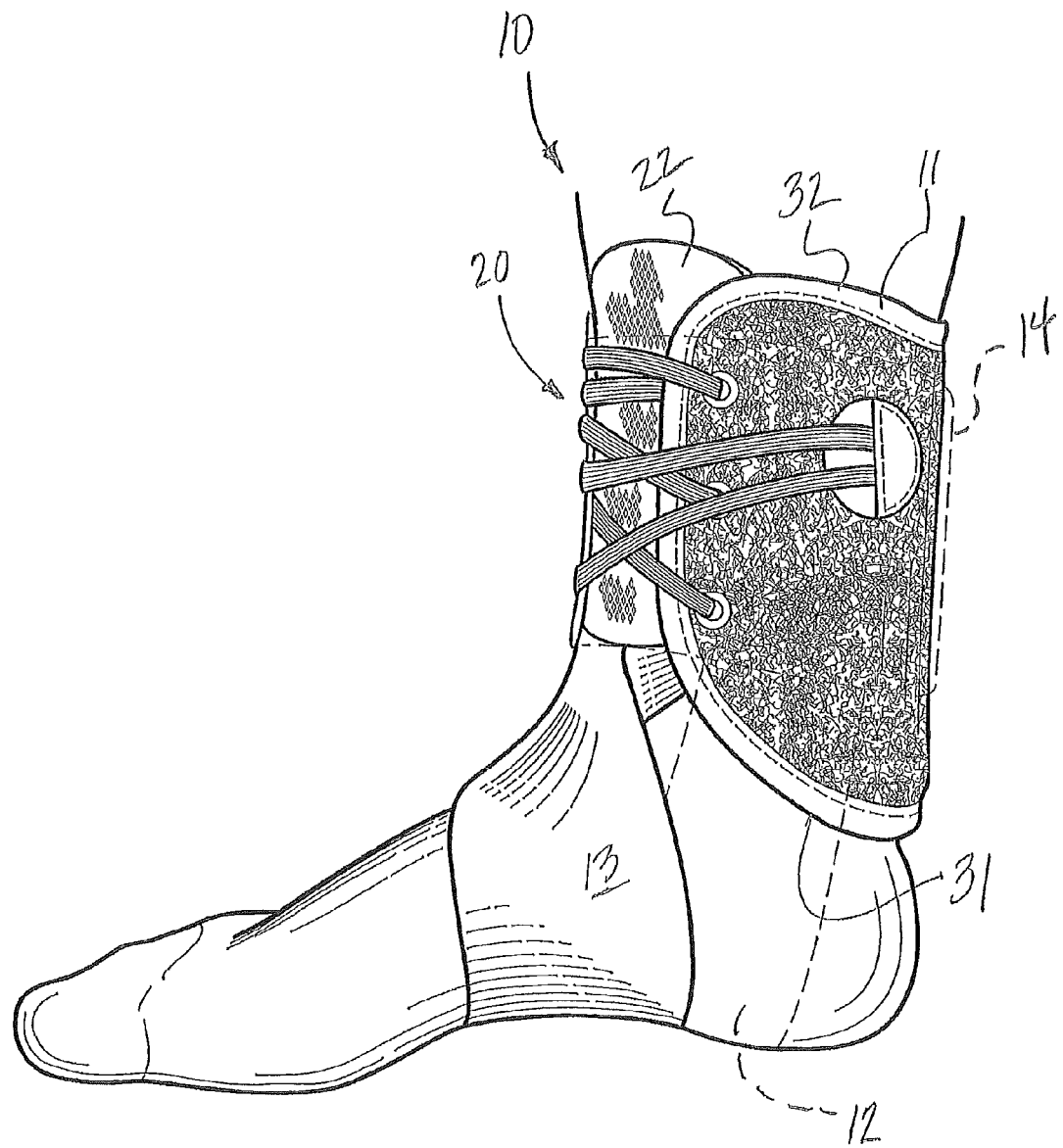
FIG. 4 is a side view of the exemplary ankle stabilizing device applied to the wearer, and showing portions of the device in phantom lines to illustrate otherwise hidden elements.

As best shown in FIG. 4, a lower edge 31 of the exemplary body member 11 extends immediately below or adjacent the lateral and medial malleolus of the foot and above the calcaneous, such that no portion of the body member 11 extends under the heel or around the foot. The stabilizing straps 12, 13 have respective proximal ends attached at the rear (or other portion) of the body member 11, and respective free ends which wrap around and under the foot in a generally "figure-8" type configuration (forming a substantially thin or low profile under-the-foot "stirrup") to effectively position and retain the body member 11 on the lower leg. The exemplary "figure-8" stabilizing straps 12, 13 in concert with the elastic binding straps 14, 15 (or cuff) may resemble traditional ankle taping (e.g., Gibney basket weave). The upper edge 32 of the body member 11 may extend above the ankle joint at a base of the tibia and fibula to cover a high-ankle area of the wearer.

Figure 5:
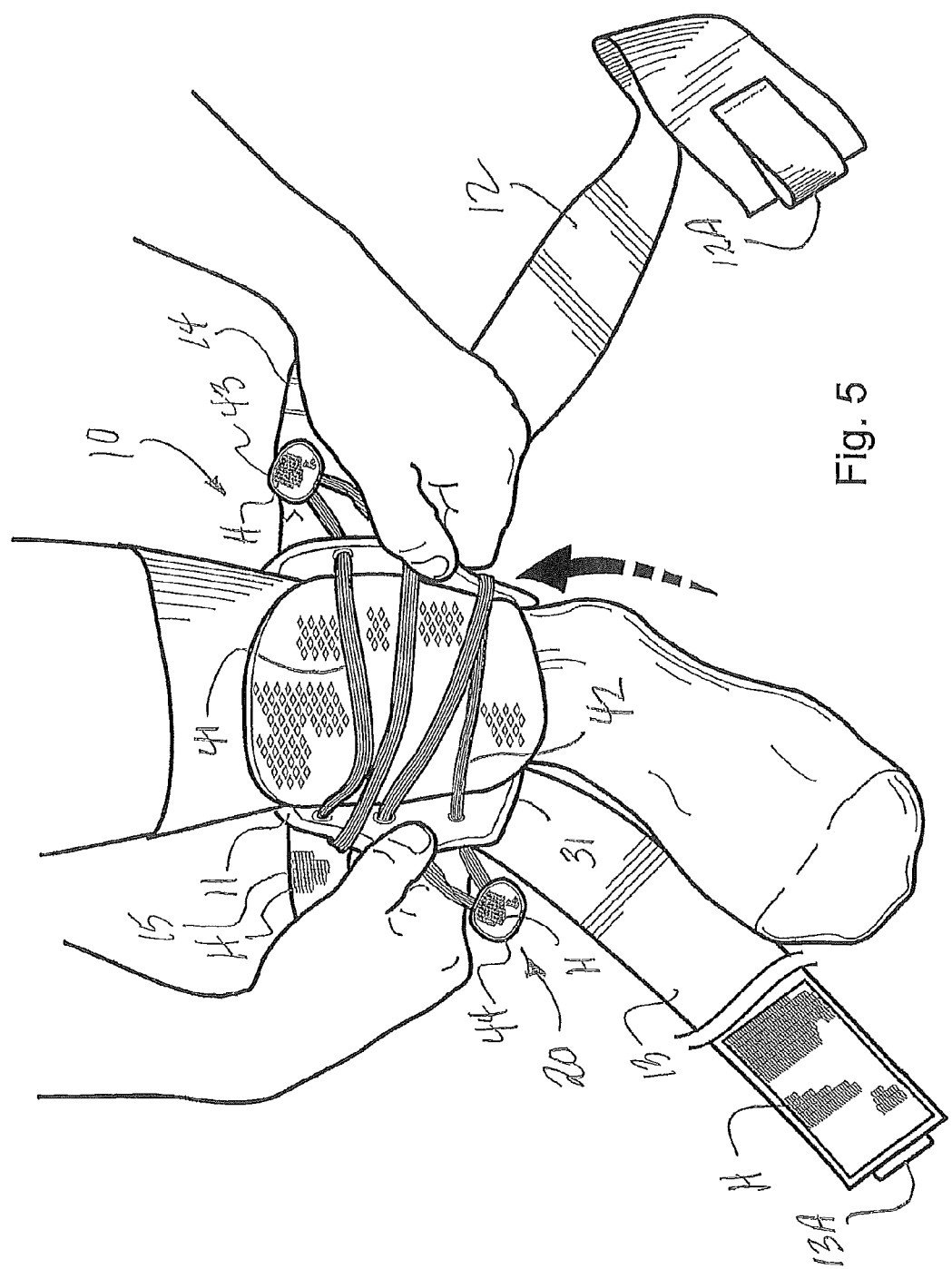
FIGS. 5-11 are views demonstrating sequential application of the exemplary ankle stabilizing device to the ankle and foot of the wearer.
Figure 6:
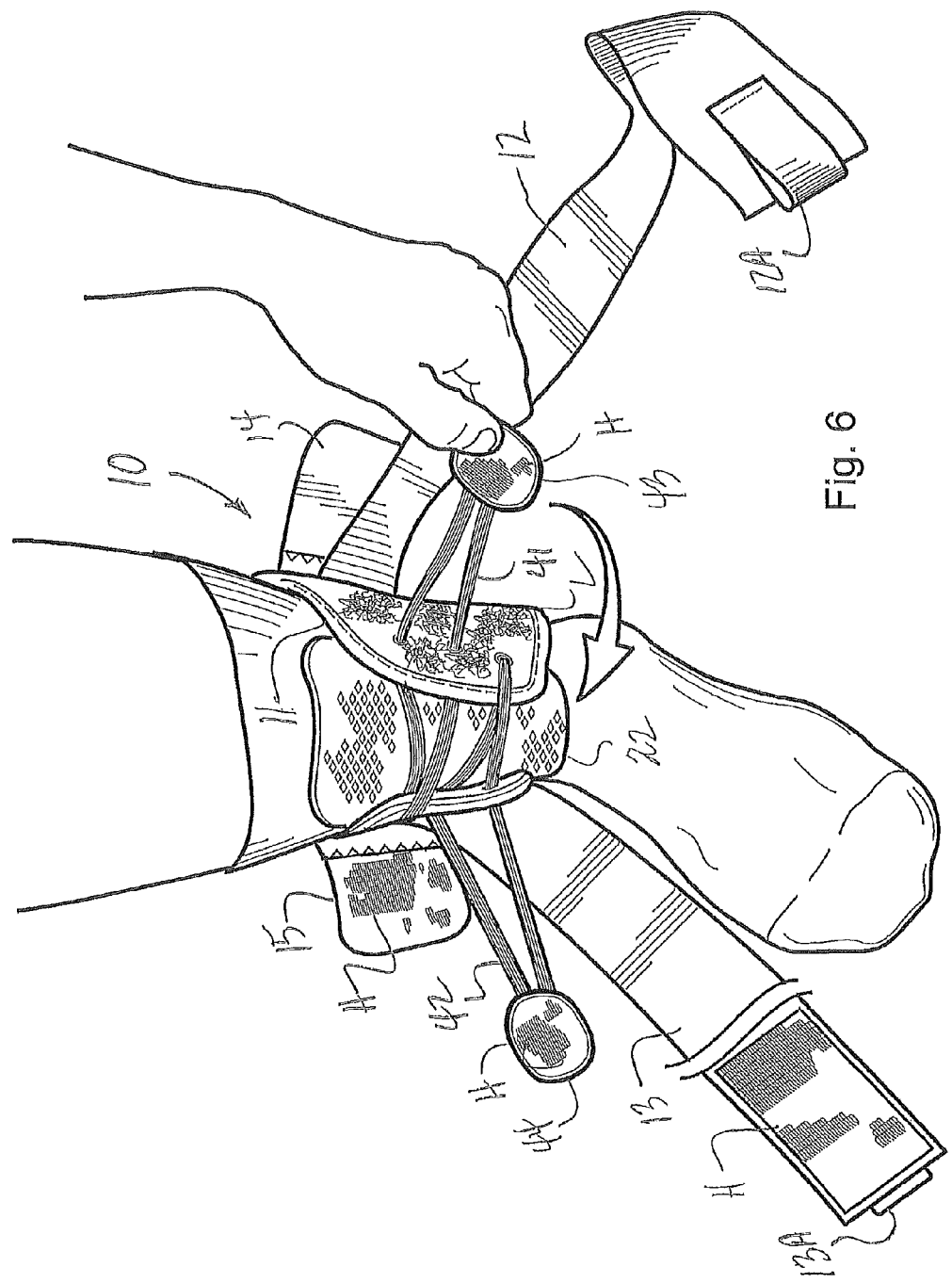
Figure 7:
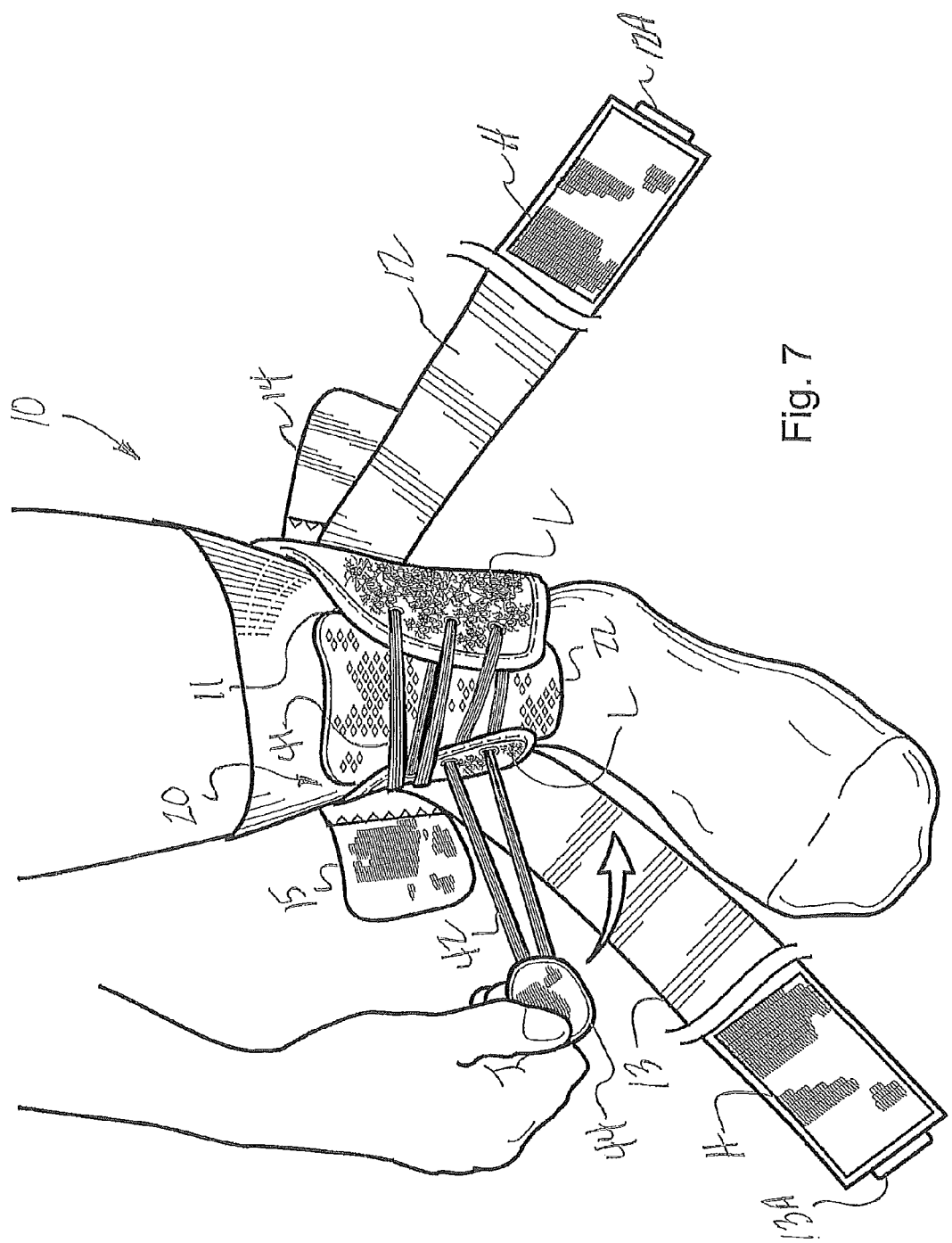
Figure 8:
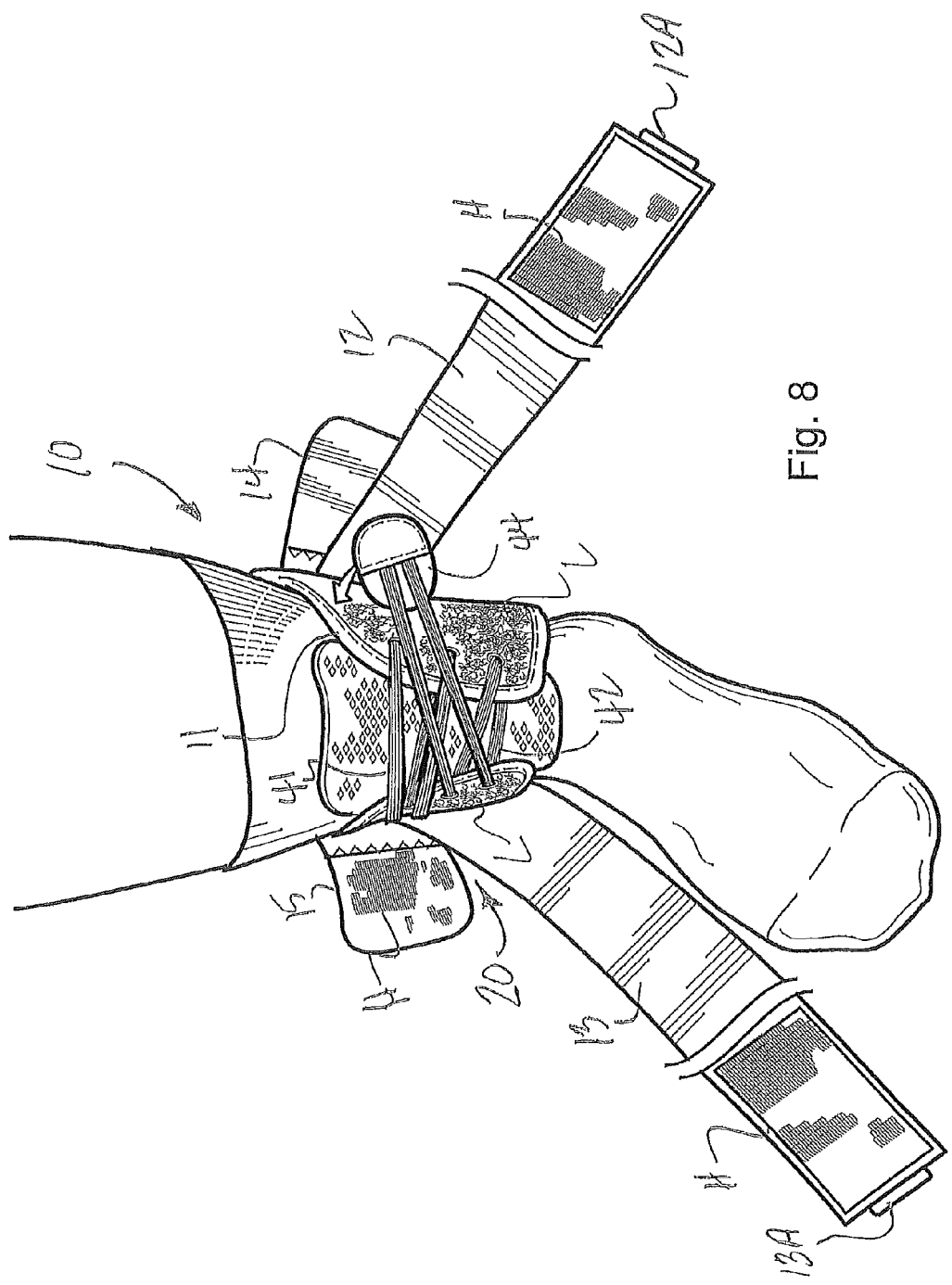

Application of the exemplary ankle stabilizing device 10 around the ankle and foot of wearer is demonstrated in sequential FIGS. 5-12. As shown in FIG. 5, the body member 11 is first placed over the wearer's foot by expanding the lace-cinch closure assembly 20, as described further below, and inserting the foot through end openings. As indicated previously, the body member 11 is located on the ankle such that its lower edge 31 resides immediately below or adjacent the lateral and medial malleolus of the foot and above the calcaneous. The laces 41, 42 of closure assembly 20 are then drawn tight, as shown in FIGS. 6, 7, and 8, by pulling the generally circular lace tabs 43, 44 outwardly away from the foot, crossing the laces 41, 42 over the perforated tongue 22 at the longitudinal front gap 21, and attaching the lace tabs 43, 44 (via hook fasteners "H") to respective areas of loop fasteners "L" formed with opposing side panels 11A, 11B of body member 11. The loop fasteners "L" may occupy entire exterior surface areas of body side panels 11A and 11B.

Figure 9:
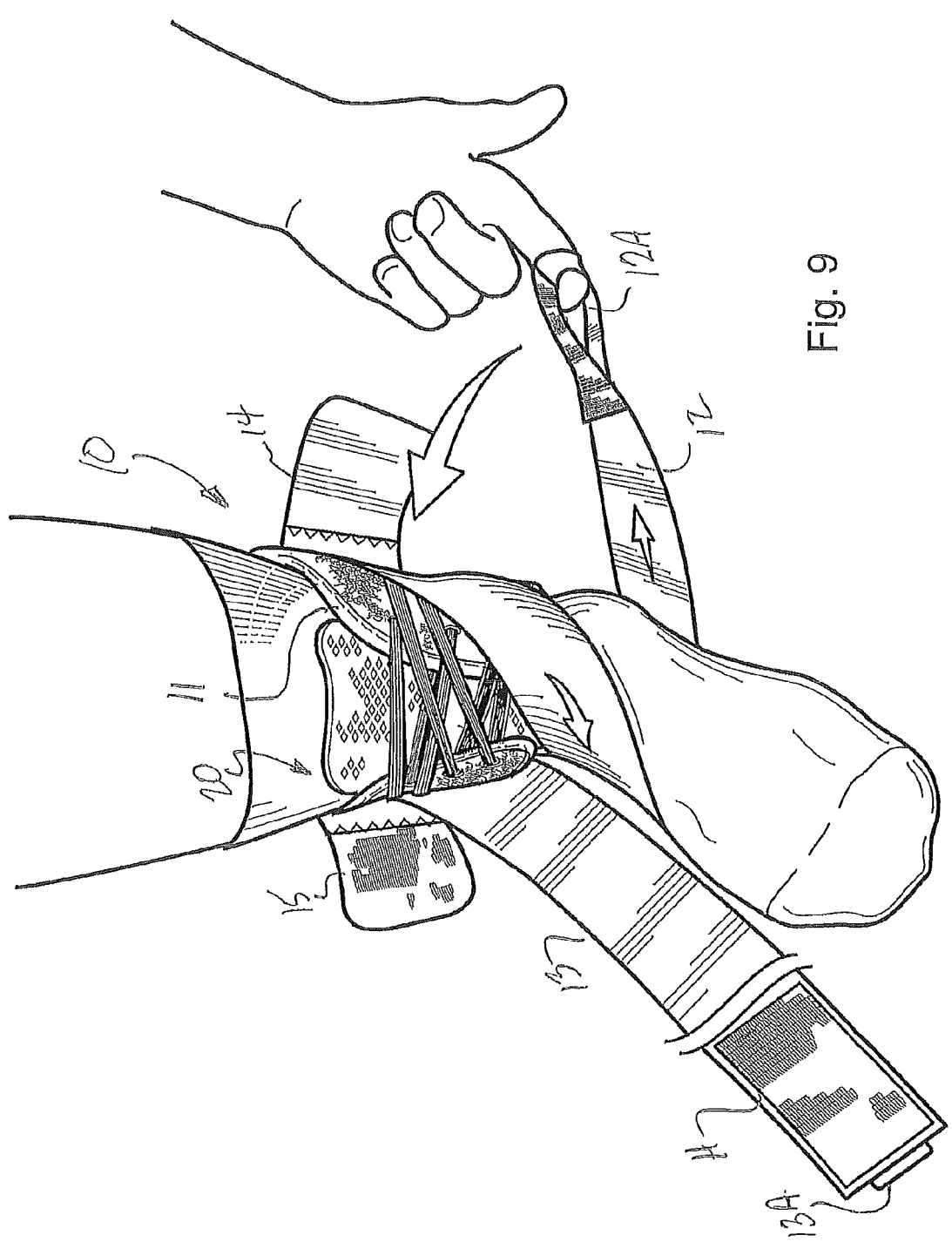
Figure 10:
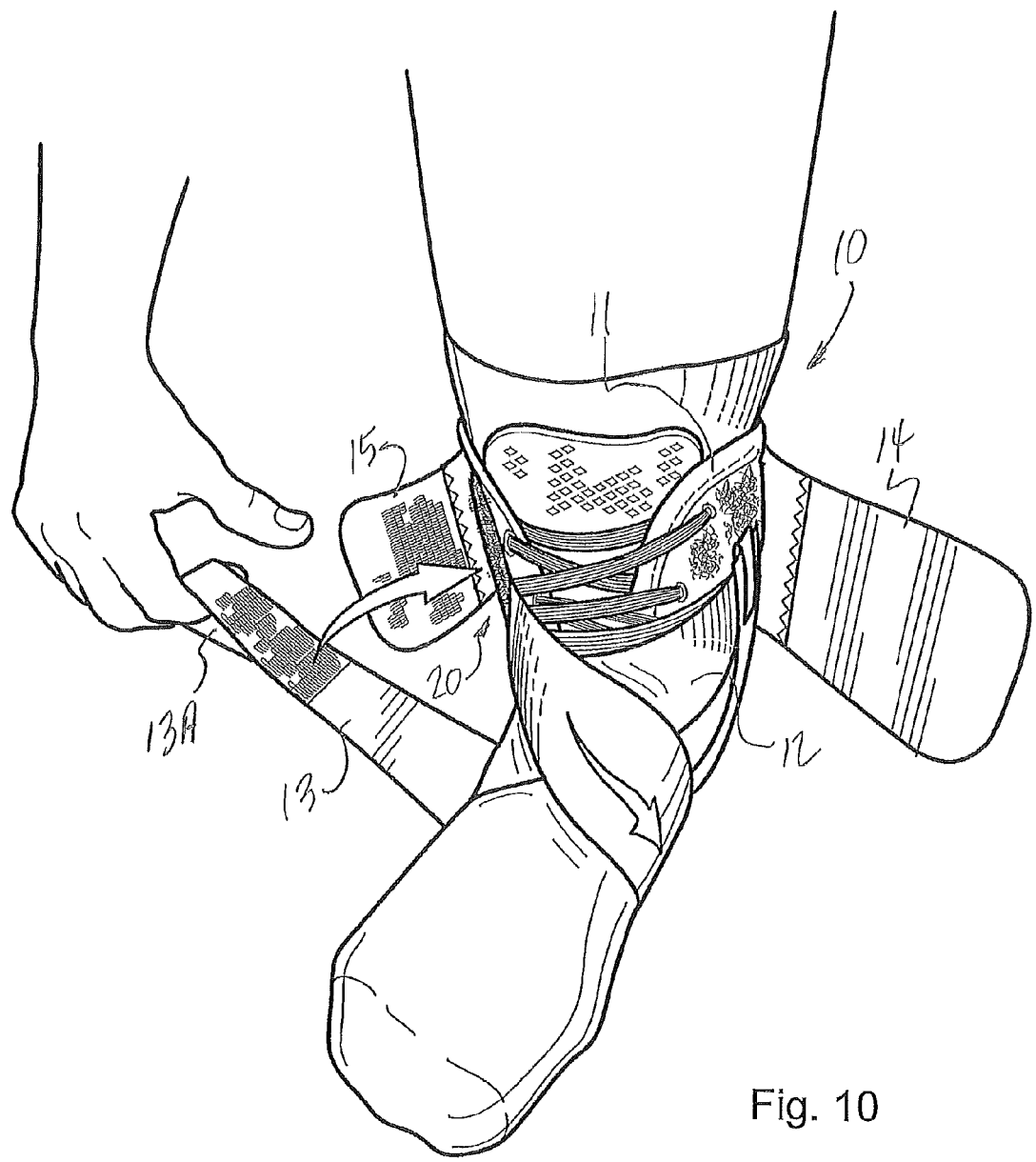
Figure 11:
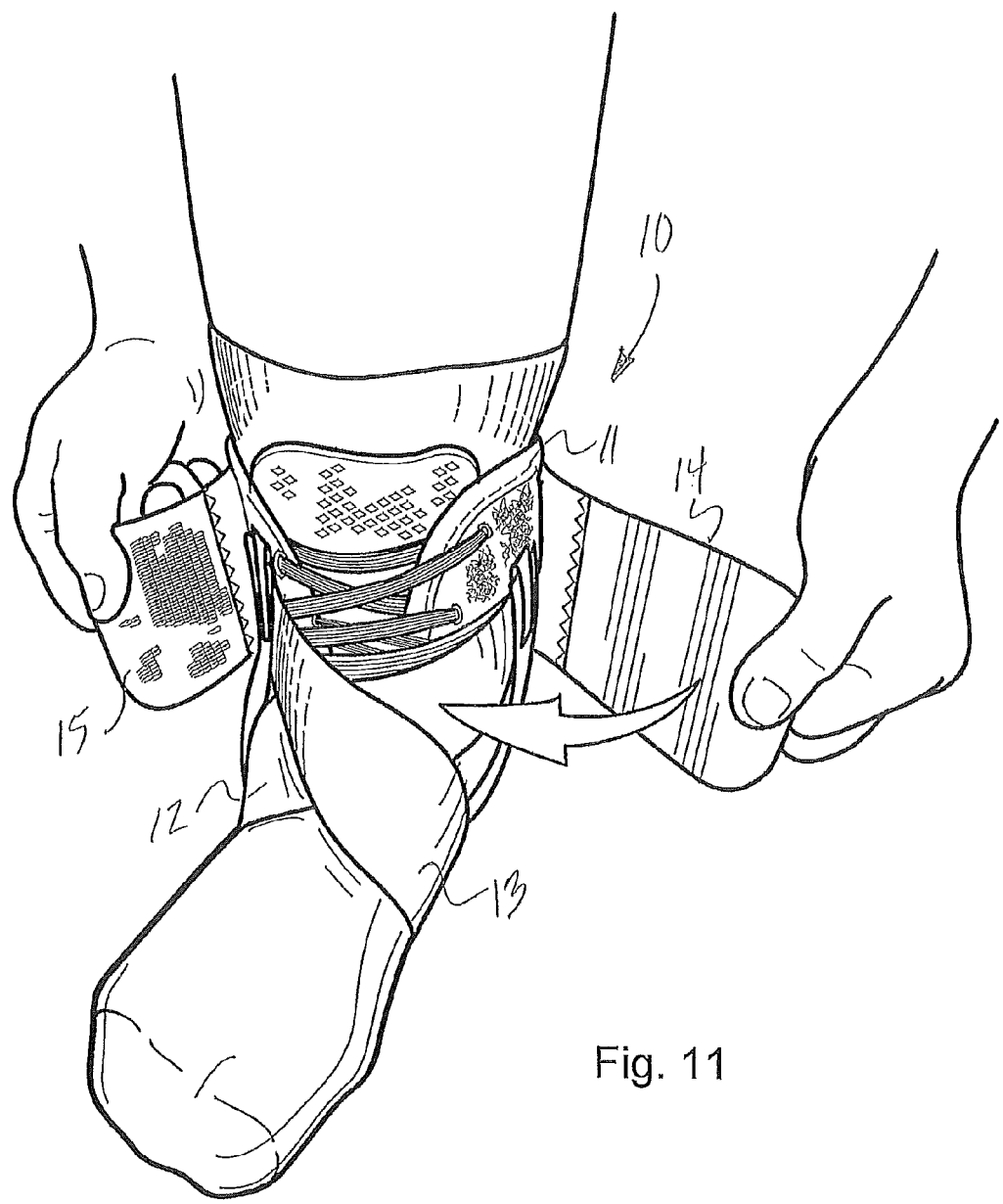
Figure 12:
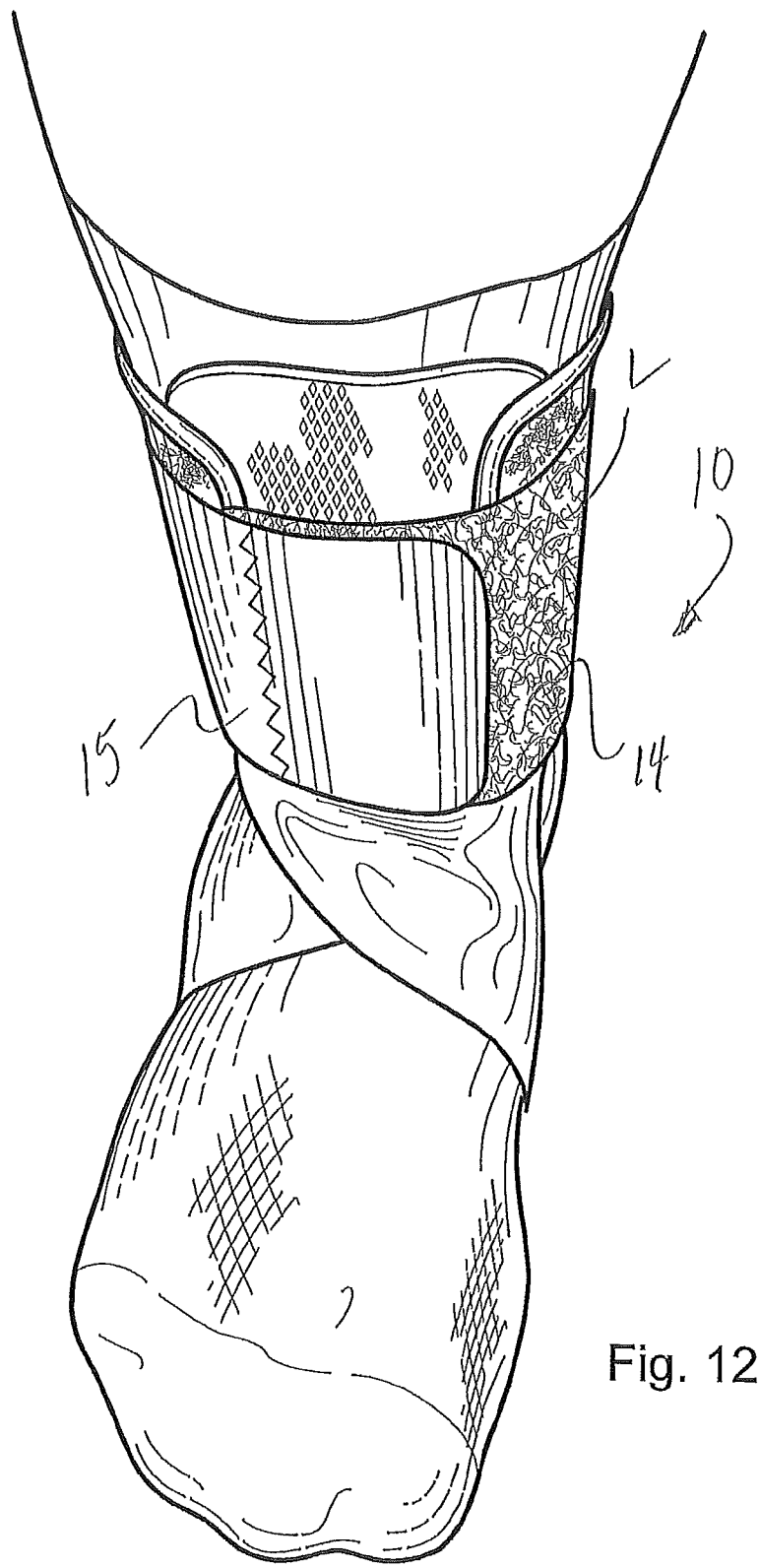
FIG. 12 is a front perspective view of the exemplary ankle stabilizing device applied to the wearer.

After the lace-cinch closure assembly 20 is suitably tightened, the wearer then wraps the stabilizing straps 12, 13 over the foot and under the heel as demonstrated in FIGS. 9 and 10 in a generally figure-8 type configuration indicated above. The straps 12, 13 may be readily handled using attached finger loops 12A, 13A. Respective free ends of the straps 12, 13 have hook fasteners "H" designed to releasably mate with the complementary loop fasteners "L" formed on opposing side panels 11A, 11B of the body member 11. Once the stabilizing straps 12, 13 are properly applied and attached, the rear-attached binding straps 14, 15 are laid over the exposed laces 41, 42 of the closure assembly 20, as indicated in FIG. 11, and attached together via additional mating hook and loop fasteners "H" and "L", FIG. 12 illustrates the exemplary ankle stabilizing device 10 applied to the ankle and foot of the wearer. In this embodiment, except for the thin stabilizing straps 12, 13 under and around the foot, no part of the exemplary ankle stabilizing device 10 covers the foot of the wearer.

Exemplary Lace-Cinch Closure Assembly 20

Figure 13A:
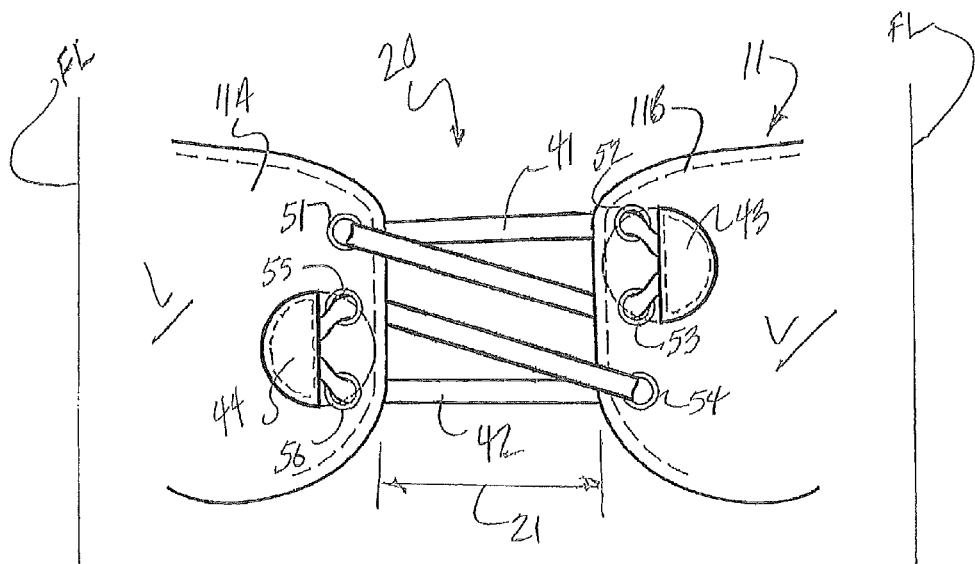
FIGS. 13A and 13B are schematic views demonstrating operation of the exemplary lace-cinch closure assembly.
Figure 13B:
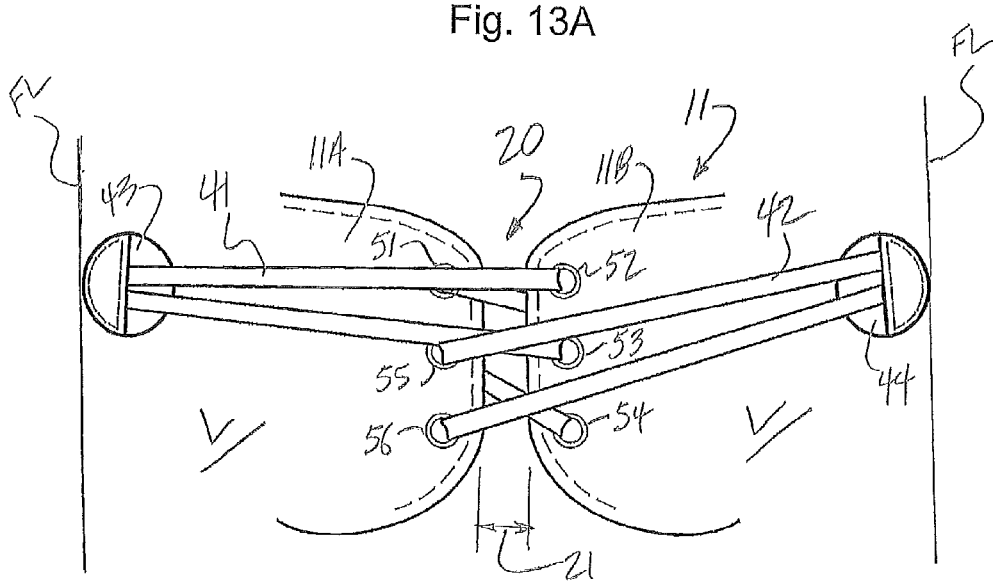
Figure 14:
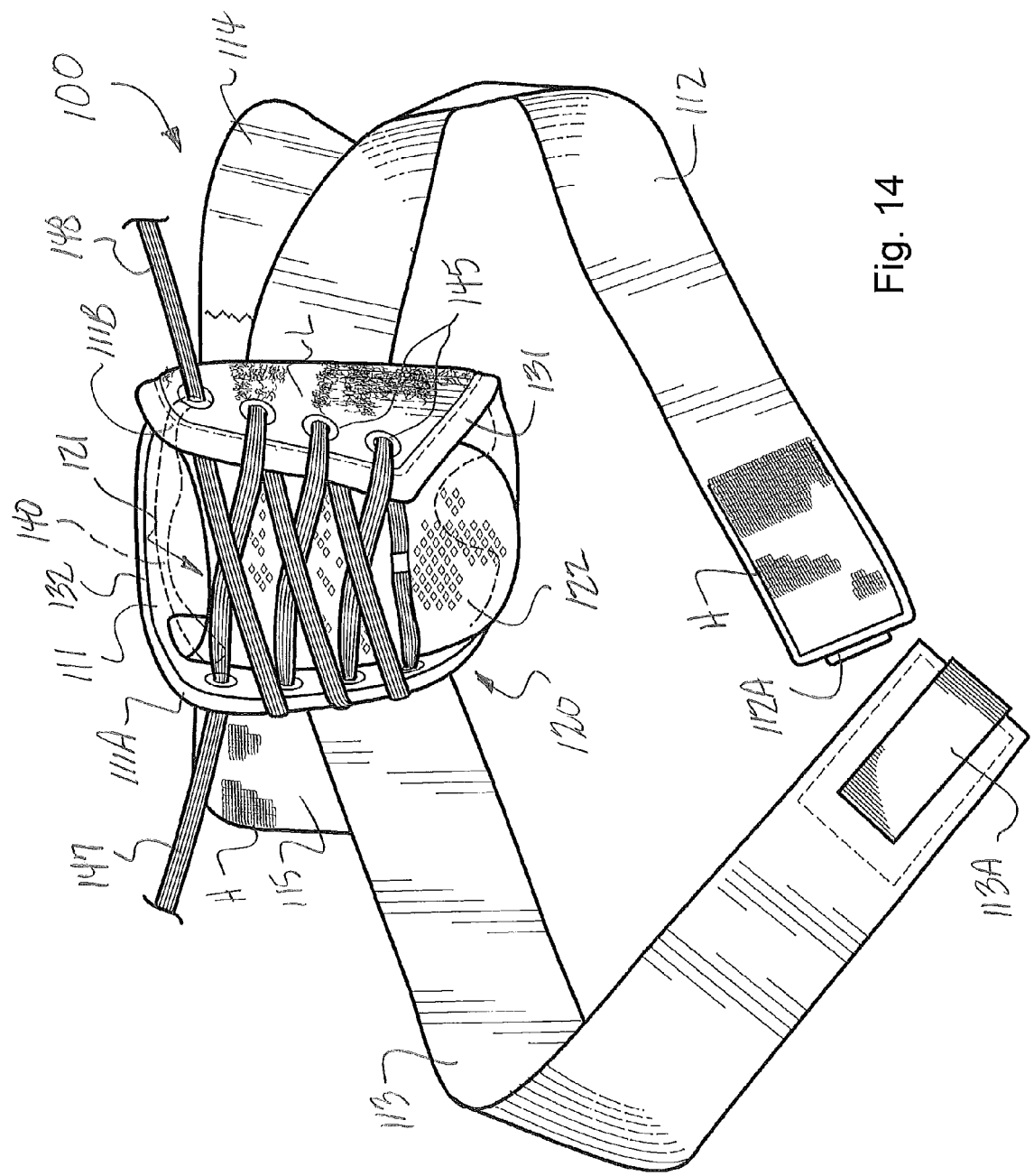
FIGS. 14 and 15 are perspective views illustrating an alternative exemplary embodiment of the present disclosure.
Figure 15:
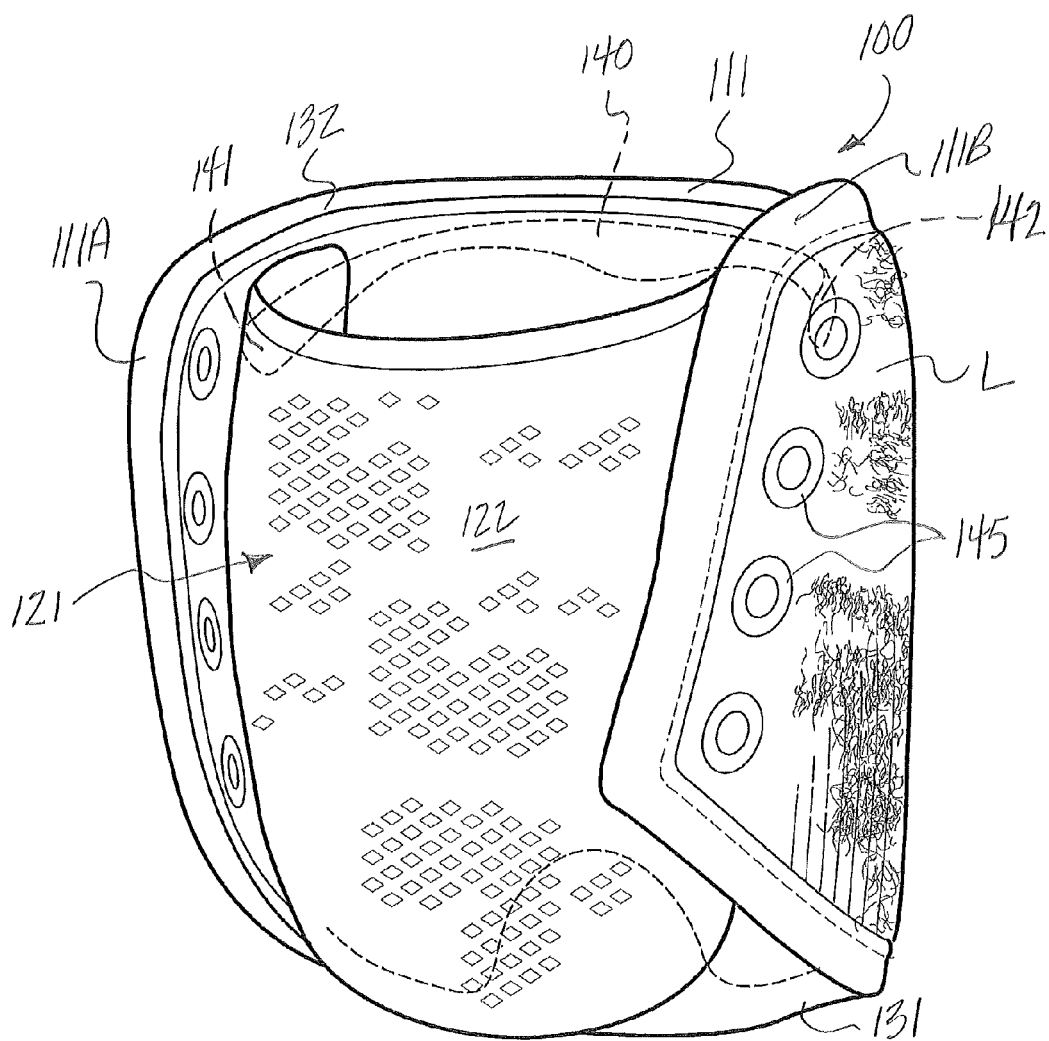

Referring again to FIG. 1, and schematic FIGS. 13A and 13B, in the exemplary ankle stabilizing device 10 the lace-cinch closure assembly 20 comprises two independently adjustable laces 41, 42 (two separate lengths) passing through brass eyelets 51-56 of body member 11, and attached at their free ends to respective lace tabs 43, 44. The exemplary lace tabs 43, 44 are generally circular, and have continuous areas of hook fasteners "H" (See FIG. 1) designed to releasably mate with the exterior loop fasteners "L" located on opposite side panels 11A, 11B of the body member 11. In the exemplary embodiment, upper lace 41 passes through a top eyelet 51 on one side panel 11A of body member 11, extends across the longitudinal front gap 21 in a generally triangular fashion, and through the upper two spaced eyelets 52, 53 on the opposite side panel 11B of body member 11. Free ends of the upper lace 41 extending through upper eyelets 52, 53 are permanently attached (e.g., by sewing or other means) to the first lace tab 43. The lower lace 42 passes through a bottom eyelet 54 on side panel 11B of body member 11, extends across the longitudinal front gap 21 in an opposite triangular fashion, and through the lower two spaced eyelets 55, 56 on side panel 11A of body member 11. Free ends of the lower lace 42 extending through lower eyelets 55, 56 are attached (e.g., by sewing or other means) to the second lace tab 44.

As indicated in FIG. 13A, the lace tabs 43, 44 are substantially larger than the eyelets 52, 53, thereby preventing complete separation of the laces 41, 42 from opposing side panels 11A, 11B of body member 11, and defining a maximum spacing (or foot-insertion opening) of the ankle stabilizing device 10. This maximum opening is sufficient to accommodate the size requirements of a particular wearer, and may meet or slightly exceed the ankle circumference around the heel—thus allowing ready application of the ankle stabilizing device 10 over the foot. Attachment of the laces 41, 42 at the center of tabs 43, 44 maximizes the allowable front gap 21, thereby maximizing the foot-insertion opening defined by the ankle stabilizing device 10, to facilitate application of the device 10 without compromising effectiveness of the lace tabs' hook fasteners "H" when the body member 11 is subsequently tightened around the ankle. To close the front gap 21, and thereby constrict the opening defined by the device 10, the lace tabs 43, 44 are pulled outwardly and apart (as indicated by arrows) and pressed onto the complementary loop fasteners "L" formed with exterior surfaces of the opposing side panels 11A, 11B. FIG. 13B shows the lace tabs 43, 44 pulled apart and releasably fastened to the body member 11 at points immediately adjacent respective outermost fastener lines "FL" (located at the rear of the device 10), thereby closing the gap 21 between the opposing side panels 11A, 11B and minimizing the opening defined by the device 10. In this case, the body member 11 is wrapped around the ankle of the wearer in its closest or tightest fitting condition.

Alternative Exemplary Embodiment

Figure 20:
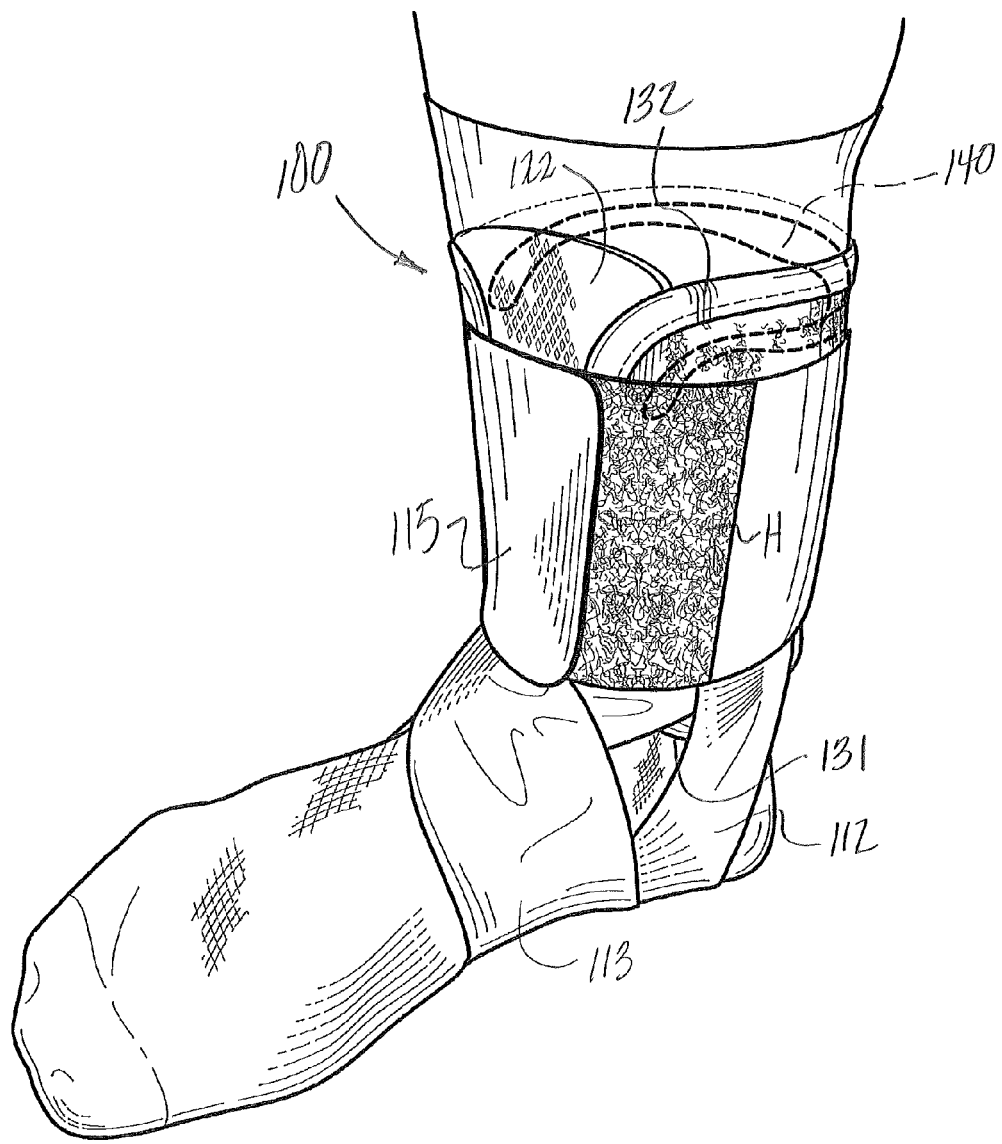
FIG. 20 illustrates the exemplary ankle stabilizing device applied to the lower leg of the wearer, and showing the flexible ankle belt in phantom lines.

FIGS. 14-20 illustrate an alternative exemplary embodiment of the present disclosure comprising many of the same elements and features incorporated in the ankle stabilizing device 10 described above. The ankle stabilizing device 100 comprises a flexible around-the-ankle body member 111, a pair of non-stretch nylon stabilizing straps 112, 113 attached at the rear (or other portion) of body member 111, and elastic rear-attached binding straps 114, 115. The stabilizing straps 112, 113 and binding straps 114, 115 may be constructed, attached, and assembled as previously described. Like the ankle stabilizing device 10, the flexible body member 111 of ankle stabilizing device 100 may be constructed of a substantially inelastic, multiple-layer woven ballistic nylon fabric. The body member 111 defines top and bottom open ends for receiving the foot of a wearer, as describe further below, and a lace-cinch closure assembly 120. The closure assembly 120 functions to adjustably close a longitudinal front gap 121 formed between opposing integrally-formed side panels 111A, 111B of body member 111, thereby adjustably tightening the body member 111 around the ankle. A perforated double, warp-knit, three-dimensional fabric tongue 122 may be attached to the body member 111 (extending between side panels 111A, 111B), and adapted to reside between the closure assembly 120 and ankle. The device may be used over a thin sock or stocking, as shown in FIG. 20, or may be applied directly to a bare ankle and foot.

Figure 16:
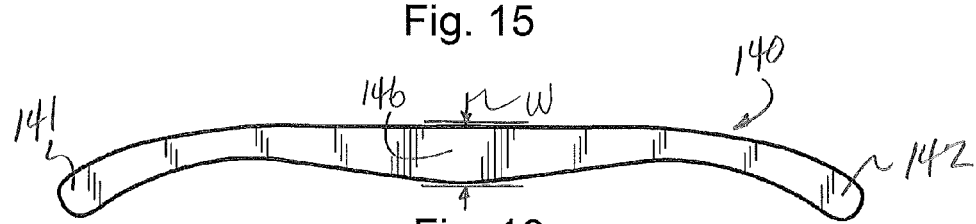
FIGS. 16 and 17 are views of the exemplary flexible ankle belt designed for placement between outside and inside layers of the around-the-ankle body member.
Figure 17:
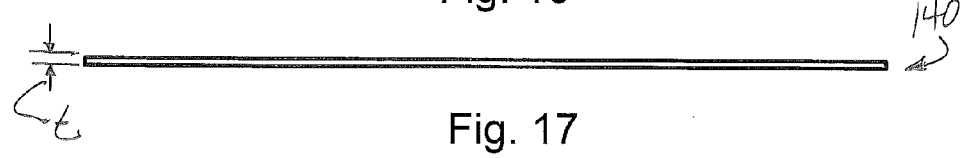
Figure 18:
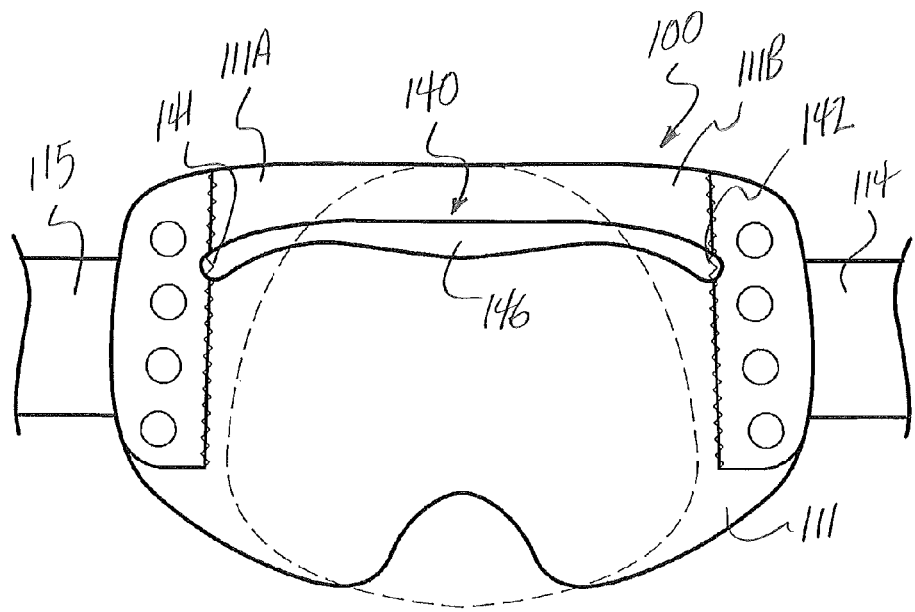
FIG. 18 illustrates one location of the flexible ankle belt on the body member, the ankle belt being sewn at its opposite ends to respective reinforcing fabric panels of the lace eyelets and to the outside layer of the body member at a center point of the belt.
Figure 19:
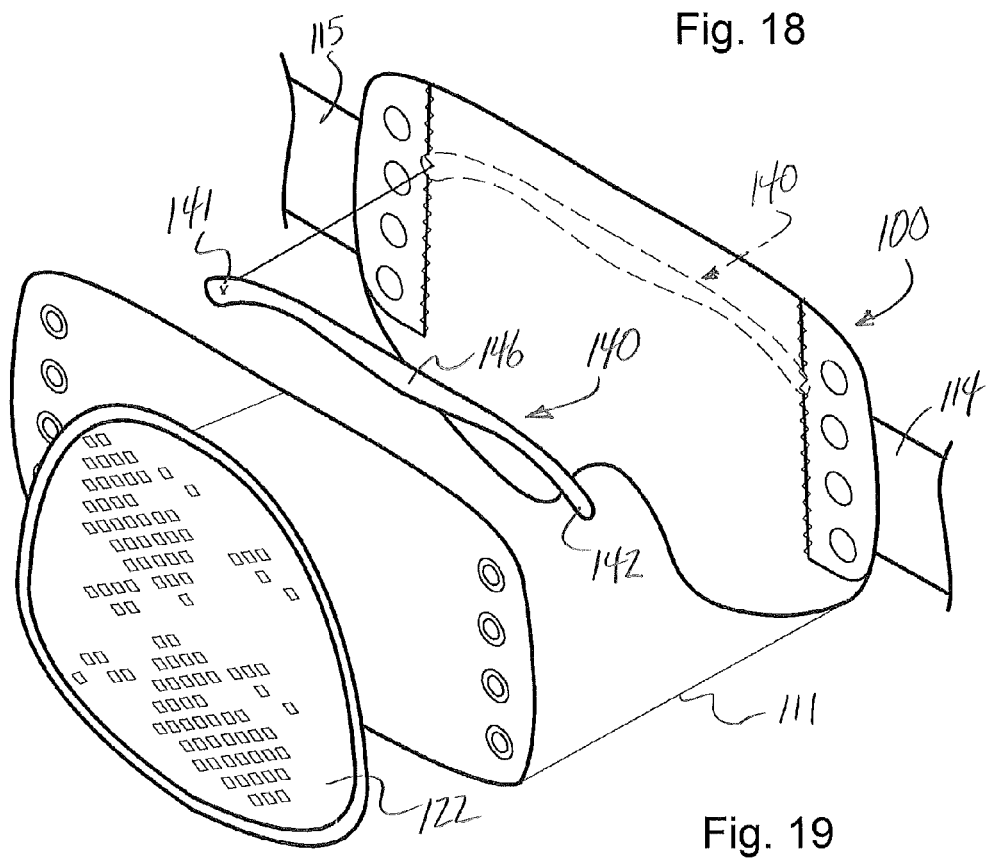
FIG. 19 is an exploded view illustrating assembly of various components of the exemplary body member relative to the flexible ankle belt.

A lower edge 131 of the exemplary body member 111 extends immediately below or adjacent the lateral and medial malleolus of the foot and above the calcaneous, such that no portion of the body member 111 extends under the heel or around the foot. The stabilizing straps 112, 113 have respective proximal ends attached at the rear (or other portion) of the body member 111, and respective free ends which wrap around and under the foot in a generally "figure-8" type configuration forming a substantially thin or low profile under-the-foot "stirrup" to effectively position and retain the body member 111 on the lower leg. Like the ankle stabilizing device 10, the exemplary "figure-8" stabilizing straps 112, 113 of ankle stabilizing device 100 in concert with the elastic binding straps 114, 115 (or cuff) may resemble traditional ankle taping (e.g., Gibney basket weave). The straps 112, 113 may be readily handled using attached finger loops 112A, 113A, Respective free ends of the straps 112, 113 have hook fasteners "H" designed to releasably mate with the complementary loop fasteners "L" formed on opposing side panels 111A, 111B of the body member 111. Once the stabilizing straps 112, 113 are properly applied and attached, the rear-attached binding straps 114, 115 are laid over the closure assembly 120, and attached together via additional mating hook and loop fasteners "H" and "L". The upper edge 132 of the body member 111 may extend above the ankle joint at a base of the tibia and fibula to cover a high-ankle area of the wearer. The exemplary ankle stabilizing device 100 incorporates a flexible non-stretch ankle belt 140 constructed of a thin plastic located between overlying inside and outside fabric layers of the body member 111, and sewn at its opposite ends 141, 142 (see FIGS. 18 and 19) to respective side panels 111A, 111B proximate the lace eyelets 145 of the device 100. The ankle belt 140 may also be sewn at or near its center point 146 to the outside fabric layer of the body member 111. In one exemplary embodiment, the thickness (t) of the ankle belt is approximately 1/32 to 1/16 inches, and its width (w) is about 1/4 to 3/8 inches. As best shown in FIG. 16, the width (w) of the exemplary ankle belt 140 is greatest at its center point 146 and tapers slightly towards opposite ends 141, 142. The ends 141, 142 may be slightly arcuate and downwardly-turned.

When the ankle stabilizing device 100 is applied to the lower leg and tightened and secured by laces 147, 148 of closure assembly 120, the flexible ankle belt 140 functions to provide a substantially 360-degree inelastic "belt effect" (or support) to help reduce distal migration of the body member 111 on the lower leg during use. The exemplary ankle belt 140 enhances the circumferential (or generally horizontal) compression applied above the malleoli of the wearer when the lace ends 147, 148 are properly tightened. The enhanced compression provided by the ankle belt 140 may further promote extended retention of stabilizing tension generated by the straps 112, 113. FIG. 20 illustrates the ankle stabilizing device 100 applied to the lower leg of the wearer, and showing the flexible ankle belt 140 extending substantially (e.g., greater than 270 degrees) around a high ankle portion of the lower leg.

For the purposes of describing and defining the present invention it is noted that the use of relative terms, such as "substantially", "generally", "approximately", and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

Exemplary embodiments of the present invention are described above. No element, act, or instruction used in this description should be construed as important, necessary, critical, or essential to the invention unless explicitly described as such. Although only a few of the exemplary embodiments have been described in detail herein, those skilled in the art will readily appreciate that many modifications are possible in these exemplary embodiments without materially departing from the novel teachings and advantages of this invention. Accordingly, all such modifications are intended to be included within the scope of this invention as defined in the appended claims.

In the claims, any means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. Unless the exact language "means for" (performing a particular function or step) is recited in the claims, a construction under §112, 6th paragraph is not intended. Additionally, it is not intended that the scope of patent protection afforded the present invention be defined by reading into any claim a limitation found herein that does not explicitly appear in the claim itself.

What is claimed:

1. An ankle stabilizing device for use on an ankle and foot of a wearer, said ankle stabilizing device comprising:
    an above-the-foot flexible body member designed to substantially encircle the ankle, and comprising an open upper end adapted for extending to a point above the ankle, and an open lower end adapted for terminating at a point above the foot;
    an elongated, flexible, non-stretch ankle belt secured to said body member proximate its upper end, and adapted for extending substantially circumferentially around a lower leg of the wearer, and said ankle belt having opposite downwardly-turned ends and a center point between the ends, and said ankle belt being wider at its center point than at each opposite end; and
    first and second elongated non-stretch stabilizing straps having respective proximal ends affixed to said body member and respective free ends, the free ends being adapted for extending under and around the foot in a generally figure-8 type configuration and releasably attaching to said body member.

2. An ankle stabilizing device according to claim 1, wherein respective free ends of said first and second stabilizing straps and said body member comprise releasably mating hook and loop fasteners.

3. An ankle stabilizing device according to claim 2, wherein said flexible body member comprises first and second integrally-formed cooperating side panels adapted for wrapping around the ankle of the wearer.

4. An ankle stabilizing device according to claim 3, and comprising means for adjustably closing a longitudinal gap between said first and second side panels, thereby adjustably fitting said body member around the ankle of the wearer.

5. An ankle stabilizing device according to claim 4, and comprising a perforated tongue residing at the longitudinal gap between said first and second side panels.

6. An ankle stabilizing device according to claim 5, wherein said means for adjustably closing comprises at least one lace.

7. An ankle stabilizing device according to claim 6, wherein said first and second side panels comprise a plurality of eyelets for receiving said lace.

8. An ankle stabilizing device according to claim 1, wherein said ankle belt has a thickness in the range of approximately 1/32 to approximately 1/16 inches, and a width in the range of approximately 1/4 to approximately 3/8 inches.

9. An ankle stabilizing device according to claim 1, wherein said ankle belt is affixed to said body member at respective opposite ends of said ankle belt.

* * * * *